United States Patent
Gondi et al.

(10) Patent No.: US 10,450,251 B2
(45) Date of Patent: Oct. 22, 2019

(54) PROCESS FOR THE PREPARATION OF 3-SUBSTITUTED CANNABINOID COMPOUNDS

(71) Applicant: e-Therapeutics plc, Oxfordshire (GB)

(72) Inventors: Vijaya Bhasker Gondi, Westford, MA (US); James Thomson Loch, III, Hopkinton, MA (US); Nicholas John Holman, Lancaster, MA (US); Steven James Collier, Concord, MA (US)

(73) Assignee: E-THERAPEUTICS PLC, Oxfordshire (GB)

( * ) Notice: Subject to any disclaimer, the term of this patent is extended or adjusted under 35 U.S.C. 154(b) by 0 days.

(21) Appl. No.: 15/780,694

(22) PCT Filed: Dec. 2, 2016

(86) PCT No.: PCT/GB2016/053795
§ 371 (c)(1),
(2) Date: Jun. 1, 2018

(87) PCT Pub. No.: WO2017/093749
PCT Pub. Date: Jun. 8, 2017

(65) Prior Publication Data
US 2018/0354876 A1    Dec. 13, 2018

Related U.S. Application Data

(60) Provisional application No. 62/263,533, filed on Dec. 4, 2015.

(51) Int. Cl.
| | | |
|---|---|---|
| C07C 29/143 | (2006.01) |
| C07C 29/48 | (2006.01) |
| C07C 35/28 | (2006.01) |
| C07C 45/64 | (2006.01) |
| C07C 49/733 | (2006.01) |
| C07D 311/80 | (2006.01) |
| C07C 67/14 | (2006.01) |
| C07C 67/29 | (2006.01) |
| C07C 45/28 | (2006.01) |
| C07F 7/18 | (2006.01) |

(52) U.S. Cl.
CPC ............ *C07C 29/143* (2013.01); *C07C 29/48* (2013.01); *C07C 35/28* (2013.01); *C07C 45/28* (2013.01); *C07C 45/64* (2013.01); *C07C 49/733* (2013.01); *C07C 67/14* (2013.01); *C07C 67/29* (2013.01); *C07D 311/80* (2013.01); *C07F 7/1804* (2013.01); *C07B 2200/07* (2013.01); *C07C 2602/42* (2017.05); *Y02P 20/55* (2015.11)

(58) Field of Classification Search
CPC ....... C07C 29/143; C07C 29/48; C07C 35/28; C07C 45/64; C07C 49/733; C07C 2602/42; C07D 311/80; C07B 2200/07
See application file for complete search history.

(56) References Cited

U.S. PATENT DOCUMENTS

| 4,157,451 A | 6/1979 | Ohloff et al. |
| 2004/0110827 A1 | 6/2004 | Aviv et al. |

OTHER PUBLICATIONS

Burnstein et al., "Synthetic Nonpsychotropic Cannabinoids with Potent Antiinflammatory, Analgesic, and Leukocyte Antiadhesion Activities", Journal of Medicinal Chemistry, 1992, 35(17), 3135-3141.
Kato et al., "Preparation of Key Intermediates for the Asymmetric Synthesis of Oxygenated Elemanoids," Journal of the Chemical Society, Perkins Transactions 1, 1993, (22), 2831-2836.
Kurose et al., "Composition of the essential oils from the leaves of nine Pinus species and the cones of three of Pinus species", Flavour and Fragrance Journal, 2007, 22(1), 10-20, published Nov. 30, 2006.
Liu et al., "Copper-Catalyzed γ-Sulfonylation of α,β-Unsaturated Carbonyl Compounds by Means of Silyl Dienol Ethers", Organic Letters, 2015, 17(14), 3572-3575.
Miyazawa et al., "Biotransformation of (−)-Verbenone by Human Liver Microsomes", Bioscience, Biotechnology & Biochemistry, 2002, 66(11), 2458-2460.
Ohloff et al., "151. Access to Optically Active Ipsdienol from Verbenone", Helvetica Chimica Acta, 1977, 60(5), 1496-1500.
Paquette et al., "Oxidative Coupling of the Enolate Anion of (1R)-(+)-Verbenone with Fe(III) and Cu(II) Salts. Two Modes of Conjoining This Bicyclic Ketone across a Benzene Ring", Journal of Organic Chemistry, 1995, 60(22), 7277-7283.
Ponomarev et al., "Synthesis and analgesic activity of new compounds combining azaadamantane and monoterpene moieties," Medical Chemical Research, 2015, 24(12), 4146-4156.
Pop et al., "Neuroprotective (+) 3S, 4S Cannabinoids With Modified 5'-Side Chain", Bioorganic and Medicinal Chemistry Letters, 1996, 6(13), 1553-1558.
Yildirim, "Biotransformation of (−)-verbenone by some fungi", Journal of Chemical Research, 2011, 35(3), 133-134.
PCT International Search Report for International Application No. PCT/GB2016/053795, dated Feb. 23, 2017, 6 pages.
PCT Written Opinion of the International Searching Authority for International Application No. PCT/GB2016/053795, dated Feb. 23, 2017, 10 pages.

*Primary Examiner* — Timothy R Rozof
(74) *Attorney, Agent, or Firm* — K&L Gates LLP

(57) ABSTRACT

There is described a method of preparing a compound of formula I, and optical isomers thereof; in which $R^1$ is hydrogen or a protecting group; said method comprising oxidizing verbenone and optical isomers thereof.

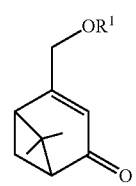

16 Claims, No Drawings

PROCESS FOR THE PREPARATION OF 3-SUBSTITUTED CANNABINOID COMPOUNDS

CROSS REFERENCE TO RELATED APPLICATIONS

This is the national phase under 35 U.S.C. § 371 of International Application No. PCT/GB2016/053795, filed on Dec. 2, 2016, which claims priority to and the benefit of U.S. Provisional Patent Application No. 62/263,533, filed on Dec. 4, 2015, the entire disclosures of each of which are incorporated by reference herein.

FIELD OF THE INVENTION

The present invention relates to a novel processes for the preparation of therapeutically active agents.

More particularly, the invention relates to a novel process for the preparation of synthetic cannabinoids, such as dexanabinol (HU-211) and HU-210.

BACKGROUND TO THE INVENTION

Dexanabinol (HU-211) is a synthetic cannabinoid derivative, but it does not act as a cannabinoid receptor agonist. Dexanabinol is the (−) enantiomer of 1,1 dimethyl heptyl-(3S,4S)-7-hydroxy-Δ$^6$-tetrahydrocannabinol also known as (6aS,10aS) 9-(hydroxymethyl)-6,6-dimethyl-3-(2-methyloctan-2-yl)-6a,7,10,10a-tetrahydrobenzo[c]chromen-1-ol and has recently become of interest due to its activity as anticancer therapy. It is the "unnatural" enantiomer of the potent cannabinoid agonist HU-210.

The (+) enantiomer, HU-210, is (6aR,10aR)-9-(hydroxymethyl)-6,6-dimethyl-3-(2-methyloctan-2-yl)-6a,7,10,10a-tetrahydrobenzo[c]chromen-1-ol 1, which is known as a potent synthetic cannabinoid.

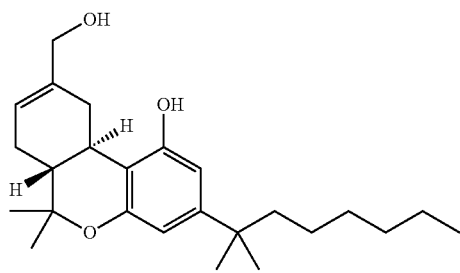

HU-210
(6aR, 10aR)-9-(Hydroxymethyl)-6,6-dimethyl-3-(2-methyloctan-2-yl)-6a,7,10,10a-tetrahydrobenzo[c]chromen-1-ol

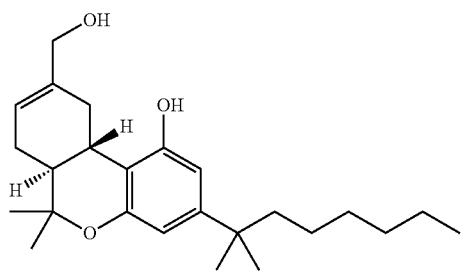

HU-211 (dexanabinol)
(6aS,10aS)-9-(Hydroxymethyl)-6,6-dimethyl-3-(2-methyloctan-2-yl)-6a,7,10,10a-tetrahydrobenzo[c]chromen-1-ol The synthetic route to high enantiomerically pure dexanabinol is described in US Patent application 2004/0110827.

The synthesis described therein (but not including (R)-verbenone) is shown schematically in Scheme 1 below:

In the known process for the synthesis of dexanabinol, a key compound is (+)-4-hydroxymyrtenol pivalate, which is coupled with dimethyheptyl resorcinol to produce dexanabinol.

However, the known synthetic route is disadvantageous in that, inter alia, stage 1 of the process requires the oxidation of (+)-α-pinene with t-butylhydroperoxide in the presence of selenium dioxide, producing a mixture of (+) myrtenol ((1R)-6,6-dimethylbicyclo[3.1.1]hept-2-ene-2-methanol) and (+) myrtenal.

Scheme 1

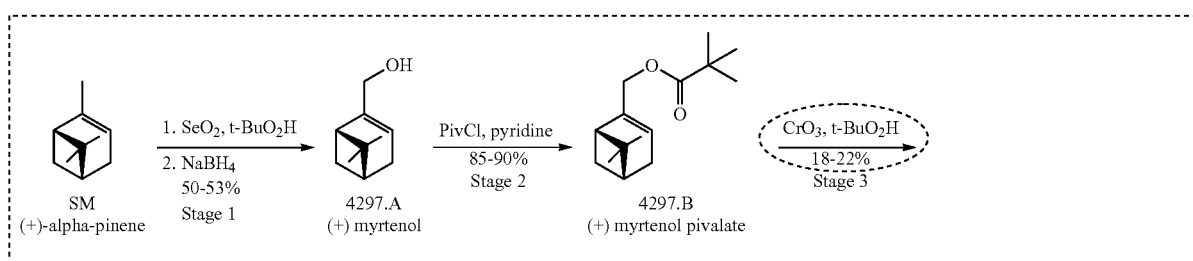

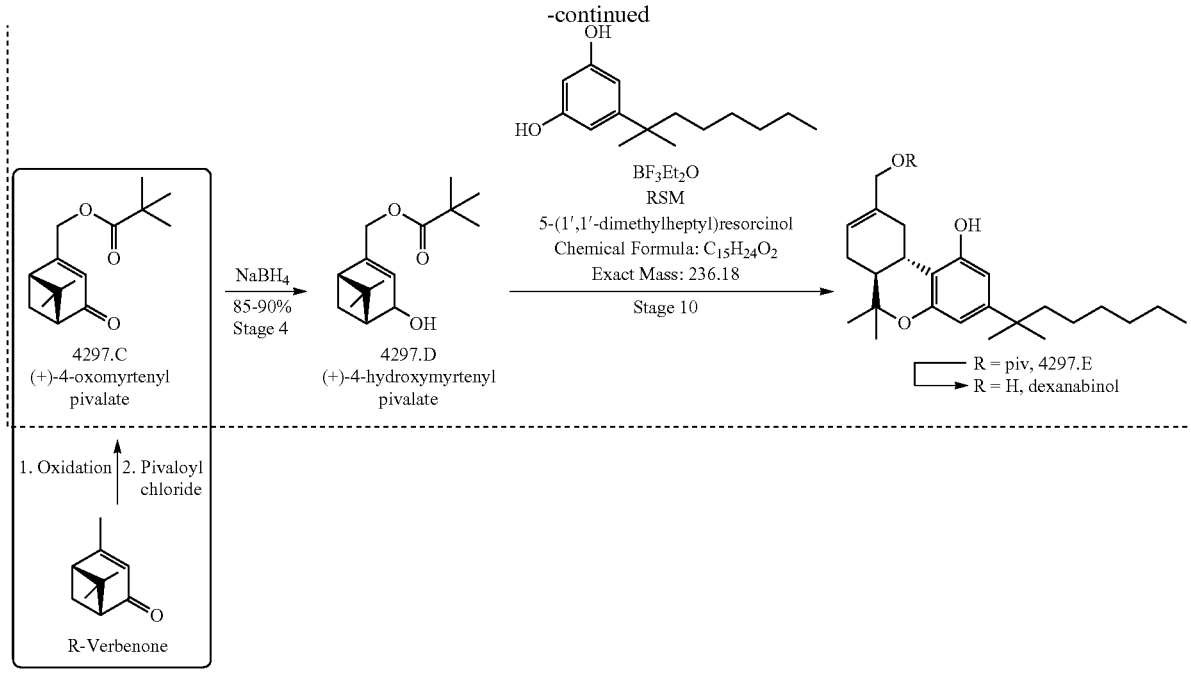

The use of selenium is very undesirable as it requires removing from the end product. Furthermore, the use of selenium dioxide requires the employment of dedicated plant equipment in order to avoid contamination. In addition, the disclosed synthetic route only produces a moderate yield.

Furthermore, the process requires allylic carbon oxidation at the internal ring carbon of (+)-myrtenol pivalate, employing chromium oxide based conditions to generate (+)-oxomyrtenol pivalate. However, the oxidation step with chromium oxide is very low yielding, ~20% and the (+)-oxomyrtenol pivalate produced is difficult to purify.

Thus, there is a need for an improved synthetic process for the manufacture of cannabinoids, such as dexanabinol and HU-210, which avoids the use of undesirable agents, such as selenium dioxide and/or chromium oxide.

We have now found a novel synthetic route for cannabinoids which overcomes or mitigates the aforementioned disadvantages and/or provides and improved yield of the desired cannabinoid, e.g. dexanabinol and HU-210.

SUMMARY OF THE INVENTION (+)-4-Oxomyrtenol and (+)-4-hydroxymyrtenol, and derivatives thereof, are key intermediates in the synthesis of 9-(hydroxymethyl)-6,6-dimethyl-3-(2-methyloctan-2-yl)-6a,7,10,10a-tetrahydrobenzo[c]chromen-1-ol cannabinoids, such as, dexanabinol and HU-210.

We have now found a novel method of preparing (+)-4-oxomyrtenol and (+)-4-hydroxymyrtenol.

Thus, according to a first aspect of the invention, there is provided a method of preparing a compound of formula I, and optical isomers thereof:

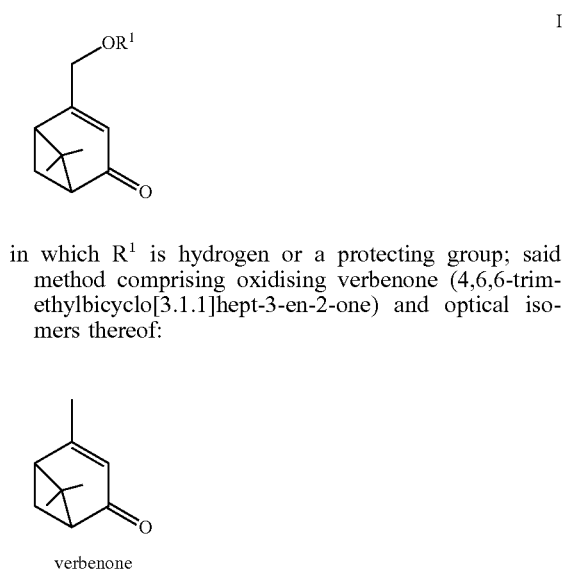

in which $R^1$ is hydrogen or a protecting group; said method comprising oxidising verbenone (4,6,6-trimethylbicyclo[3.1.1]hept-3-en-2-one) and optical isomers thereof:

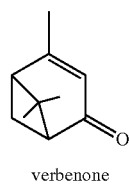

verbenone and, when $R^1$ is hydrogen, optionally protecting the product.

The oxidisation of verbenone may produce a compound of formula I in which $R^1$ is hydrogen or a protecting group. When $R^1$ is hydrogen, i.e. 4-oxomyrtenol, in which case the oxidation may optionally be followed by protection of (+)-4-oxomyrtenol.

It will be understood that oxidation of (R)-verbenone may suitably be used in the synthesis of dexanabinol. Whereas (S)-verbenone may suitably be used in the synthesis of HU-210.

The intermediates (+)-4-oxomyrtenol and (+)-4-hydroxymyrtenol may also be useful in the synthesis of other 3-substituted cannabinoid compounds.

Therefore, according to a further aspect of the invention there is provided a method of preparing a 3-substituted cannabinoid compound which comprises reacting a compound of formula I in with 5-substituted resorcinol, e.g. a 5-alkyl resorcinol.

A compound of formula I as herein described may be reacted with 5-(1,1-dimethylheptyl)resorcinol to produce a 9-(hydroxymethyl)-6,6-dimethyl-3-(2-methyloctan-2-yl)-6a,7,10,10a-tetrahydrobenzo[c]chromen-1-ol cannabinoid.

When $R^1$ is hydrogen a compound of formula I may be reacted directly, i.e. in unprotected form, with 5-(1,1-dimethylheptyl)resorcinol to produce a 9-(hydroxymethyl)-6,6-dimethyl-3-(2-methyloctan-2-yl)-6a, 7,10,10a-tetrahydrobenzo[c]chromen-1-ol cannabinoid directly.

Therefore, the present invention also provides a method of preparing a 9-(hydroxymethyl)-6,6-dimethyl-3-(2-methyloctan-2-yl)-6a, 7,10,10a-tetrahydrobenzo[c]chromen-1-ol cannabinoid which comprises reacting a compound of formula I in which $R^1$ is hydrogen, with 5-(1,1-dimethylheptyl) resorcinol.

When $R^1$ is a protecting group, the reaction of a compound of formula I with 5-(1,1-dimethylheptyl)resorcinol may produce a protected form of 9-(hydroxymethyl)-6,6-dimethyl-3-(2-methyloctan-2-yl)-6a,7,10,10a-tetrahydrobenzo[c]chromen-1-ol cannabinoid, in which case a deprotection step may be employed to yield the desired cannabinoid.

Thus, according to a further aspect of the invention there is provided a method of preparing a 9-(hydroxymethyl)-6,6-dimethyl-3-(2-methyloctan-2-yl)-6a,7,10,10a-tetrahydrobenzo[c]chromen-1-ol cannabinoid which comprises the steps of:
(i) oxidising a verbenone and optical isomers thereof:

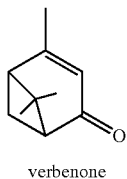

verbenone to produce 4-oxomyrtenol or protected 4-oxomyrtenol;
(ii) optionally protecting the hydroxy group of 4-oxomyrtenol;
(iii) reacting the 4-oxomyrtenol, or a protected derivative thereof, with 5-(1,1-dimethylheptyl)resorcinol to produce 9-(hydroxymethyl)-6,6-dimethyl-3-(2-methyloctan-2-yl)-6a,7,10,10a-tetrahydrobenzo[c]chromen-1-ol cannabinoid, or a protected derivative thereof; and
(iv) optionally deprotecting the protected derivative of 9-(hydroxymethyl)-6,6-dimethyl-3-(2-methyloctan-2-yl)-6a,7,10,10a-tetrahydrobenzo[c]chromen-1-ol cannabinoid.

In one aspect of the invention the cannabinoid is (6aS,10aS)-9-(hydroxymethyl)-6,6-dimethyl-3-(2-methyloctan-2-yl)-6a,7,10,10a-tetrahydrobenzo[c]chromen-1-ol, dexanabinol. The cannabinoid dexanabinol will generally be prepared using (R)-verbenone.

According to this aspect of the invention there is provided a method of preparing dexanabinol which comprises the steps of:
(i) oxidising (R)-verbenone to produce (+)-4-oxomyrtenol or protected 4-oxomyrtenol;
(ii) optionally protecting the hydroxy group of (+)-4-oxomyrtenol;
(iii) reacting the (+)-4-oxomyrtenol, or a protected derivative thereof, with 5-(1,1-dimethylheptyl)resorcinol to produce dexanabinol, or a protected derivative thereof; and
(iv) optionally deprotecting the protected derivative of dexanabinol.

According to one aspect of the invention (+)-4-oxomyrtenol is reacted with 5-(1,1-dimethylheptyl)resorcinol to produce dexanabinol.

According to another aspect of the invention a protected derivative of a (+)-4-oxomyrtenol, e.g. (+)-4-hydroxymyrtenol ester, such as 4-oxo-myrtenol pivalate ester, is reacted with 5-(1,1-dimethylheptyl)resorcinol to produce dexanabinol.

In another aspect of the invention the cannabinoid is (6aR,10aR)-9-(hydroxymethyl)-6,6-dimethyl-3-(2-methyloctan-2-yl)-6a, 7,10,10a-tetrahydrobenzo[c]chromen-1-ol, HU-210. The cannabinoid HU-210 will generally be prepared using (S)-verbenone.

According to a yet further aspect of the invention there is provided a method of preparing HU-210 which comprises the steps of:
(i) oxidising (S)-verbenone to produce (−)-4-oxomyrtenol or protected 4-oxomyrtenol;
(ii) optionally protecting the hydroxy group of (−)-4-oxomyrtenol;
(iii) reacting the (−)-4-oxomyrtenol, or a protected derivative thereof, with 5-(1,1-dimethylheptyl)resorcinol to produce HU-210, or a protected derivative thereof; and
(iv) optionally deprotecting the protected derivative of HU-210.

According to one aspect of the invention (−)-4-oxomyrtenol is reacted with 5-(1,1-dimethylheptyl)resorcinol to produce HU-210.

According to another aspect of the invention a protected derivative of a (−)-4-oxomyrtenol, e.g. (−)-4-hydroxymyrtenol ester, such as 4-oxo-myrtenol pivalate ester, is reacted with 5-(1,1-dimethylheptyl)resorcinol to produce HU-210.

When $R^1$ is a protecting group, it may generally comprise any such protecting group known to the person skilled in the art for protection against oxidation. Such protecting groups include, but shall not be limited to, acetic acid ester, acetonide, allyl ether, benzoic acid ester, benzyl ether, benzylidene acetal, t-butyl ether, t-butyldimethylsilyl ether, t-butyldiphenylsilyl ether, methoxymethyl ether, pivalic acid ester, tetrahydropyranyl ether; and the like. In a particular aspect of the invention $R^1$ is a pivalic acid ester moiety.

The oxidisation of verbenone to compound of formula I as herein described may be via a dienol intermediate of formula II, and optical isomers thereof:

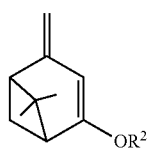

II in which $R^2$ is a protecting group.

Compounds of formula II and optical isomers thereof are novel per se. Therefore, according to a yet further aspect of the invention there is provided compounds of formula II and optical isomers thereof:

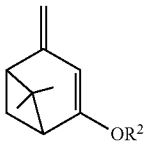

in which R² is a protecting group.

Thus, in one aspect of the invention the compound of formula II is the (R)-isomer IIa:

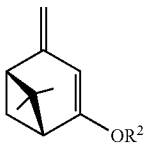

in which R² is as herein defined.

In another aspect of the invention the compound of formula II is the (S)-isomer IIb:

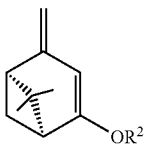

in which R² is as herein defined.

The invention further provides the use of a compound of formula II and optical isomers thereof in the manufacture of a 9-(hydroxymethyl)-6,6-dimethyl-3-(2-methyloctan-2-yl)-6a, 7,10,10a-tetrahydrobenzo[c]chromen-1-ol cannabinoid.

According to this aspect of the invention there is provided the use of a compound of formula II in the manufacture of (6aS,10aS)-9-(hydroxymethyl)-6,6-dimethyl-3-(2-methyloctan-2-yl)-6a,7,10,10a-tetrahydrobenzo[c]chromen-1-ol, dexanabinol.

There is also provided the use of a compound of formula II in the manufacture of (6aR,10aR)-9-(hydroxymethyl)-6,6-dimethyl-3-(2-methyloctan-2-yl)-6a,7,10,10a-tetrahydrobenzo[c]chromen-1-ol, HU-210.

Thus, according to a further aspect of the invention there is provided a method of preparing a 9-(hydroxymethyl)-6,6-dimethyl-3-(2-methyloctan-2-yl)-6a,7,10,10a-tetrahydrobenzo[c]chromen-1-ol cannabinoid which comprises the steps of:
(i) oxidising a compound of formula II and optical isomers thereof;

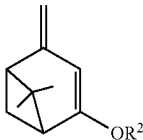

in which R² is a protecting group;
to produce 4-oxomyrtenol or protected 4-oxomyrtenol;

(ii) optionally protecting the hydroxy group of 4-oxomyrtenol;
(iii) reacting the 4-oxomyrtenol, or a protected derivative thereof, with 5-(1,1-dimethylheptyl)resorcinol to produce 9-(hydroxymethyl)-6,6-dimethyl-3-(2-methyloctan-2-yl)-6a,7,10,10a-tetrahydrobenzo[c]chromen-1-ol cannabinoid, or a protected derivative thereof; and
(iv) optionally deprotecting the protected derivative of 9-(hydroxymethyl)-6,6-dimethyl-3-(2-methyloctan-2-yl)-6a,7,10,10a-tetrahydrobenzo[c]chromen-1-ol cannabinoid.

In one aspect of this method of the invention the cannabinoid is (6aS,10aS)-9-(hydroxymethyl)-6,6-dimethyl-3-(2-methyloctan-2-yl)-6a,7,10,10a-tetrahydrobenzo[c]chromen-1-ol, dexanabinol.

In another aspect of this method of the invention the cannabinoid is (6aR,10aR)-9-(hydroxymethyl)-6,6-dimethyl-3-(2-methyloctan-2-yl)-6a,7,10,10a-tetrahydrobenzo[c]chromen-1-ol, HU-210.

According to this aspect of the invention the compounds of formula II as hereon defined may be prepared by oxidising verbenone. The compound of formula II may be an isolated intermediate or it may be prepared in situ.

Thus, the method as herein described may comprise an initial step of oxidation of verbenone to produce 4-oxomyrtenol.

The oxidising of verbenone to produce a compound of formula II may comprise a vinylogous rubottom oxidation. A rubottom oxidation will generally comprise silyl enol ether formation with subsequent rearrangement and oxidisation. A suitable reagent for silyl enol ether formation may be tert-butyldimethylsilyl trifluoromethanesulfonate (TBSOTf), although it will be understood by the person skilled in the art that other silylating agents may be utilised.

Such silylating agents include, but shall not be limited to, trimethylsilanes, such as, allyltrimethylsilane, N,O-bis(trimethylsilyl)acetamide, N,O-bis(trimethylsilyl)carbamate, N,N-bis(trimethylsilyl)formamide, N,N-bis(trimethylsilyl)methylamine, bis(trimethylsilyl) sulfate, N,O-bis(trimethylsilyl)trifluoroacetamide, N,N'-bis(trimethylsilyl)urea, (ethylthio)trimethylsilane, ethyl trimethylsilylacetate, hexamethyldisilane, hexamethyldisilazane, hexamethyldisiloxane, hexamethyldisilthiane, (isopropenyloxy)trimethylsilane, 1-methoxy-2-methyl-1-trimethylsiloxypropene, (methylthio)trimethylsilane, methyl 3-trimethylsiloxy-2-butenoate, N-methyl-N-trimethylsilylacetamide, methyl trimethylsilylacetate, N-methyl-N-trimethylsilylheptafluorobutyramide, N-Methyl-N-trimethylsilylheptafluorobutyramide (MSHFBA), N-methyl-N-trimethylsilyltrifluoroacetamide, (phenylthio)trimethylsilane, trimethylbromosilane, trimethylchlorosilane, trimethyliodosilane, 4-trimethylsiloxy-3-penten-2-one, N-(trimethylsilyl)acetamide (TMS-acetamide), trimethylsilyl acetate, trimethylsilyl azide, trimethylsilyl benzenesulfonate, trimethylsilyl cyanide (TMSCN), N-(trimethylsilyl)diethylamine (TMSDEA), N-(trimethylsilyl)dimethylamine (TMSDMA), trimethylsilyl N,N-dimethylcarbamate (DMCTMS), 1-(trimethylsilyl)imidazole (TMSIM), trimethylsilyl methanesulfonate, 4-(trimethylsilyl)morpholine, 3-trimethylsilyl-2-oxazolidinone (TMSO), trimethylsilyl perfluoro-1-butanesulfonate, trimethylsilyl nonaflate, trimethylsilyl trichloroacetate, trimethylsilyl trifluoroacetate, trimethylsilyl trifluoromethanesulfonate and trimethylsilyl trifluoromethanesulfonate.

The present invention further provides 9-(hydroxymethyl)-6,6-dimethyl-3-(2-methyloctan-2-yl)-6a,7,10,10a-tetrahydrobenzo[c]chromen-1-ol cannabinoid or a salt or ester thereof, prepared according to the process herein described.

According to one aspect of the invention there is provided (6aS,10aS)-9-(hydroxymethyl)-6,6-dimethyl-3-(2-methyl-octan-2-yl)-6a, 7,10,10a-tetrahydrobenzo[c]chromen-1-ol, dexanabinol, prepared according to the process herein described.

In another aspect of the invention there is provided (6aR,10aR)-9-(hydroxymethyl)-6,6-dimethyl-3-(2-methyl-octan-2-yl)-6a,7,10,10a-tetrahydrobenzo[c]chromen-1-ol, HU-210 prepared according to the process herein described.

As used herein, the term "salt" shall mean a "pharmaceutically acceptable salt" and refers to salts that retain the biological effectiveness and properties of the compounds of this invention and, which are not biologically or otherwise undesirable. Similarly, the "ester" shall mean a "pharmaceutically acceptable ester".

Salts are desirably pharmaceutically acceptable base addition salts, which can be formed with inorganic and organic bases. Inorganic bases from which salts can be derived include, for example, sodium, potassium, lithium, ammonium, calcium, magnesium, iron, zinc, copper, manganese, aluminium, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesised by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like). Such reactions are typically carried out in water or in an organic solvent, or in a mixture of the two. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Other salts include ammonium or amino acid salts which are water soluble thereby being preferred. Complex salts with basic amino acids can be used directly and mixed salts with neutral or acidic amino acids are previously converted into the alkali metal, alkaline earth metal or ammonium salts. Other methods also known for medicaments, in which the active material is adsorbed onto aluminium oxide gels, can also be carried out. Amino acid salts may comprise an essential amino acid, such as, histidine, isoleucine, leucine, lysine, methionine, phenylalanine, threonine, tryptophan, valine and tyrosine; or a non-essential amino acid, such as, alanine, arginine, aspartate, cysteine, glutamate, glutamine, glycine, proline, serine, asparagines and selenocysteine. Alternatively, the salt may comprise an amino sugar, such as meglumine.

Esters will generally be pharmaceutically acceptable esters which may be produced by reacting the parent compound with an appropriate alcohol. Esters of pharmaceutically acceptable alcohols can be formed with organic alcohols, such esters include, but shall not be limited to, e.g. acetate, acetoxyethyl ester (axetil), aspartate, benzoate, besylate, camsylate, cinnamate, citrate, edisylate, esylate, ethanesulfonate, formate, fumarate, gluceptate, gluconate, glucuronate, glycolate, hexafluorophosphate, hibenzate, isethionate, lactate, malate, maleate, malonate, mandelate, mesylate, methanesulfonate, methylsulphate, 2-napsylate, naphthylate, nicotinate, orotate, oxalate, palmitate, pamoate, pivalate, propionate, pyruvate, saccharate, salicylate, stearate, succinate, tartrate, p-toluenesulfonate, tosylate, trifluoroacetate, and the like.

The invention will now be described by way of example only and with reference to the accompanying figures, in which:

FIG. 1 is the $^1$H NMR for the pivalate ester of 4-oxo-myrtenol or hydroxyl verbenone (RTE 1.2B) prepared by the method of Example 1 a);

FIG. 2 is the FTIR for the pivalate ester of 4-oxo-myrtenol or hydroxyl verbenone (RTE 1.2B) prepared by the method of Example 1a);

FIG. 3 is the $^1$H NMR for the pivalate ester of 4-oxo-myrtenol or hydroxyl verbenone prepared by the prior art method of Scheme 1 herein; and FIG. 4 is the FTIR for the for the pivalate ester of 4-oxo-myrtenol or hydroxyl verbenone prepared by the prior art method of Scheme 1 herein.

EXAMPLE 1

1a) Pivalation of 4-oxo-myrtenol (RTE.1.1)

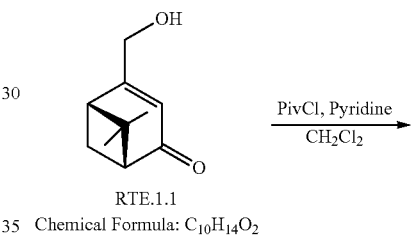

RTE.1.1
Chemical Formula: $C_{10}H_{14}O_2$
Molecular Weight: 166.22

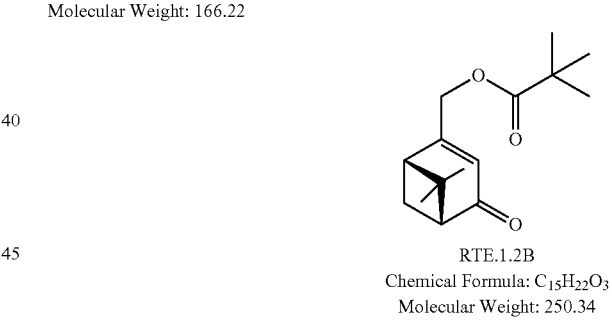

RTE.1.2B
Chemical Formula: $C_{15}H_{22}O_3$
Molecular Weight: 250.34

4-Oxo-myrtenol (RTE.1.1) was protected as the pivalate ester on a 1.0 g scale as follows:

The 4-oxo-myrtenol (RTE.1.A.1) (Lot#2213-162-3, 76% wt/wt; 1.0 g, 4.6 mmoles) was charged into a 40 mL scintillation vial with septum and nitrogen inlet. The vial was charged with $CH_2Cl_2$ (5 mL, 5 volumes) and the suspension was cooled with an ice/salt bath. The vial was then charged with pyridine (0.56 mL, 1.5 equivs). Next the vial was charged with pivaloyl chloride (0.68 mL, 1.2 equivs) dropwise by syringe. The reaction was allowed to warm gradually and was stirred overnight. The following morning the progress was checked by TLC and the starting alcohol appeared to be consumed giving a new major spot at higher Rf.

The reaction was then quenched with ice bath cooling by the gradual addition of 1 N HCl solution (5 mL, 5 volumes). The reaction was allowed to warm with vigorous stirring. The layers were separated by pipet and the bottom layer ($CH_2Cl_2$, product) was set aside. The aqueous layer was then extracted 1× with $CH_2Cl_2$ (5 mL, 5 volumes.) The combined organic layers were then washed with water (5 mL, 5 volumes.) The organic layers were then washed with saturated sodium bicarbonate (5 mL, 5 volumes) followed by washing with brine solution (5 mL, 5 volumes.) The $CH_2Cl_2$ layer was then concentrated (Rotovap, 30-40° C.). The resulting amber yellow oil was then analysed.

LC-2213-166-1 Major peak 17.010 mins (69.85%) plus smaller peak 21.214 mins (22.89%).

GC-MS-2213-166-1 Major peak 8.459 mins (parent ion not seen) Minor peak 8.886 mins.

LC-MS-2213-166-1 Major peak 6.083 mins (ES+ 251) second peak 7.067 mins.

NMR ($CDCl_3$)-2213-166-2 $^1H$ supports desired structure with fairly good purity.

The crude product was taken up in $CH_2Cl_2$ and transferred to a silica flash column. Elution with a 0-5-10% ethyl acetate/$CH_2Cl_2$ step gradient gave the product in good purity. The fractions were combined and concentrated (Rotovap, 30-40° C.) Residual solvent was chased with portions of $CH_2Cl_2$ to yield a viscous, nearly colourless oil (0.95 g, 82.5%.)

LC-2213-166-4 Major peak 17.236 mins (94.95%) plus smaller peak 18.815 mins (4.05%).

LC-MS-2213-166-4 Major peak 6.100 mins (96.39%, ES$^-$ 251 and 501) Minor peak 6.487 mins (3.61%, ES$^+$ 267).

NMR ($CDCl_3$)-[Lot #2213-158-1] $^1H$ supports desired structure with good purity (94.7% by integration of olefin proton; only a trace of residual $CH_2Cl_2$.

$^1H$ NMR pivalate ester of 4-oxo-myrtenol or hydroxyl verbenone:

300 MHz NMR, $CDCl_3$ solvent; 5.86 (1H, s, olefinic proton), 4.72 (2H, m), 2.84-2.91 (1H, m), 2.70 (1H, m), 2.45 (1H, m), 2.16 (1H, d, 9 Hz), 1.53 (3H, s), 1.25 (9H, s), 1.04 (3H, s).

The $^1H$ NMR for the pivalate ester of 4-oxo-myrtenol or hydroxyl verbenone (RTE 1.2B) is provided in FIG. 1.

The FTIR for the pivalate ester of 4-oxo-myrtenol or hydroxyl verbenone (RTE 1.2B) is provided in FIG. 2.

1b) Reduction of the Pivalate Intermediate (RTE.1.2B) to (+)-4-hydroxymyrtenol pivalate (RTE.1.2C)

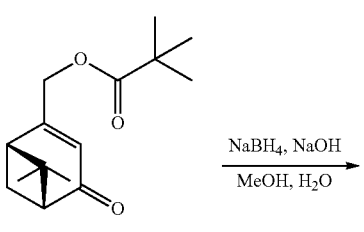

RTE.1.2B
Chemical Formula: $C_{15}H_{22}O_3$
Molecular Weight: 250.34

NaBH$_4$, NaOH
MeOH, H$_2$O

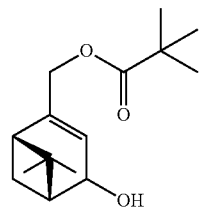

RTE.1.2C
Chemical Formula: $C_{15}H_{24}O_3$
Molecular Weight: 252.35

Reduction of 4-oxo-myrtenol pivalate ester (RTE.1.2B.) was reduced with NaBH$_4$ as follows:

A 40 mL scintillation (equipped with magnetic stirring and nitrogen inlet) was charged with 4-oxo-myrtenol pivalate ester (RTE.1.2B) (Lot#2213-166-4, 95% LC purity; 0.94 g, 3.57 mmoles). The flask was then charged with methanol (5 mL, 5 volumes) and cooled with an ice bath. The vial was charged with 40 µL of 2.5% sodium hydroxide solution. Sodium borohydride (0.067 g, 0.5 equivs) was taken up in water (0.47 mL, 0.5 volumes, basified with 20 µL of 2.5% sodium hydroxide.) The solution was charged dropwise by syringe into the cooled reaction. The reaction was allowed to warm gradually to room temperature. An aliquot was withdrawn and quenched in water with a couple of drops of 2.5% NaOH added. The aqueous layer was extracted with a small volume of $CH_2Cl_2$ and this was checked by TLC (ethyl acetate/n-heptane systems) after 2.5 hours. Only a trace of starting material remained giving a major new spot at lower Rf.

The amber reaction was cooled once again with an ice bath and a charge of acetone (0.5 mL) was added gradually by syringe. The reaction was allowed to warm and was stirred for another 1 hour.

The vial was charged with $CH_2Cl_2$ (10 mL) followed by 2.5% NaOH (1 mL). After stirring to hydrolyse any borate esters the reaction was charged with saturated sodium bicarbonate (4 mL). The layers were stirred vigorously and then allowed to settle. The bottom layer ($CH_2Cl_2$, product) was drawn off by pipet. Another 5 mL of $CH_2Cl_2$ was added and the basic layer was back extracted with this.

The combined organic layers were washed with saturated brine solution (5 mL). After stirring vigorously the layers were separated. The organic layer was concentrated (Rotovap, 30-40° C.) to give an amber oil with some white crystals. The aqueous layers were checked by TLC and there seemed to be only a trace of the major product spot.

NMR ($CDCl_3$)-2213-170-1 Supported the desired crude product structure.

LC-2213-170-2 Major peak 17.664 mins (82.49%).

LC-MS-2213-170-2 Major peak 6.161 mins (79.78%) (no parent ion).

Elution with 5-30% ethyl acetate/heptane gave the major spot in what appeared to be very good purity. Fractions were combined for concentration (Rotovap, 50° C.) After transferring to a tared vial with $CH_2Cl_2$ and additional chases obtained 0.57 g of viscous, nearly colourless oil. Lot 2213-170-3.

LC-2213-170-5 Major peak 17.672 mins (93.62%).

LC-MS-2213-170-5 Major peaks 6.166 mins (92.50%) (no parent ion.)

NMR ($CDCl_3$)-2213-170-6 $^1H$ supports desired structure with good purity. Two potencies by wt/wt using 1,4-dimethoxy benzene were performed. 2213-170-6

A&B gave an average of 84.1% for calculated yield of 53%.

The reduction proceeded without any issues and provided the coupling partner for the next step.

1c) Coupling of (+)-4-hydroxymyrtenol pivalate (RTE.1.2C) with ((1R)-6,6-Dimethylbicyclo[3.1.1]hept-2-ene-2-methanol (DMHR)

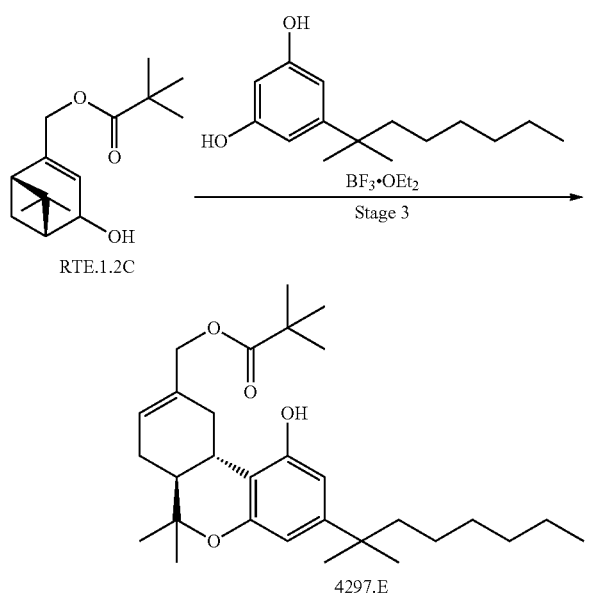

(+)-4-hydroxymyrtenol pivalate (RTE.1.2C) was subjected to the coupling reaction with dimethylbicyclo[3.1.1]hept-2-ene-2-methanol (DMIHR) as follows:

(+)-4-hydroxymyrtenol pivalate (RTE.1.2C) (Lot#2213-170-3, 84.1%; 0.28 g, 0.86 mmoles, 1.0 equiv) was charged into a 40 mL scintillation vial with septum and nitrogen inlet. The vial was charged with dimethylbicyclo[3.1.1]hept-2-ene-2-methanol (DMIHR) (260 mg, 1.2 equiv). Next the vial was charged with $CH_2Cl_2$ (5 mL) and the suspension was cooled with an ice/salt bath. The reaction was then charged with $BF_3$·etherate (0.42 mL, 3.5 equivs) added dropwise over 2 minutes by syringe. The resulting brown solution was then stirred cold for 30 mins (reaching a bath temperature of −11° C.). An aliquot was withdrawn and quenched in a small volume of water. After extracting with $CH_2Cl_2$ progress was checked by TLC in 3 systems (all ethyl acetate/heptane). There appeared to be no RTE.1.2C remaining. There was unreacted DMHR well separated from the new spot.

The reaction was then quenched in the cold by gradual addition of water (5 mL, 5 volumes). The reaction was allowed to warm with vigorous stirring. The layers were separated by pipet and the bottom layer ($CH_2Cl_2$, product) was set aside. The aqueous layer was then extracted 1× with $CH_2Cl_2$ (5 mL, 5 volumes.) The combined organic layers were then washed with saturated sodium bicarbonate (5 mL, 5 volumes.) Next the organic layers were washed with 25% sodium hydroxide (0.5 mL). After separating these layers the organic layers were adjusted to pH of ~1 with dropwise addition of 1 N HCl. Then the layers were washed 2× with water (5 mL). The organic layers then concentrated (Rotovap, 30-40° C.).

The crude product was taken up in $CH_2Cl_2$ and a few drops of methanol and transferred to a silica flash column. Elution with starting at 0-10% ethyl acetate/heptane gave elution of product well separated from DMHR and partially from two spots just above and below the major. Fractions containing the product spot were concentrated (Rotovap, 50° C.). The material was transferred to a tared vial and residual solvents were chased with portions of $CH_2Cl_2$.

LC-2213-172-1 Major peak 33.983 mins (75.25%) plus minor peak 35.125 mins (15.98%).

LC-MS-2213-172-2 Major peak 9.420 mins (88.69% at 210 nm, ES⁻ 413 loss of t-butyl).

NMR ($CDCl_3$)-2213-172-1 $^1$H supports desired structure with good apparent purity. Potency determination by wt/wt (1,4-dimethoxybenzene) as 2213-172-4

A&B gave average of 77.7%. Yield 0.26 g or calculated 50% from potency data (Lot#2213-172-3).

1d) Pivalate Deprotection to Prepare Dexanabinol

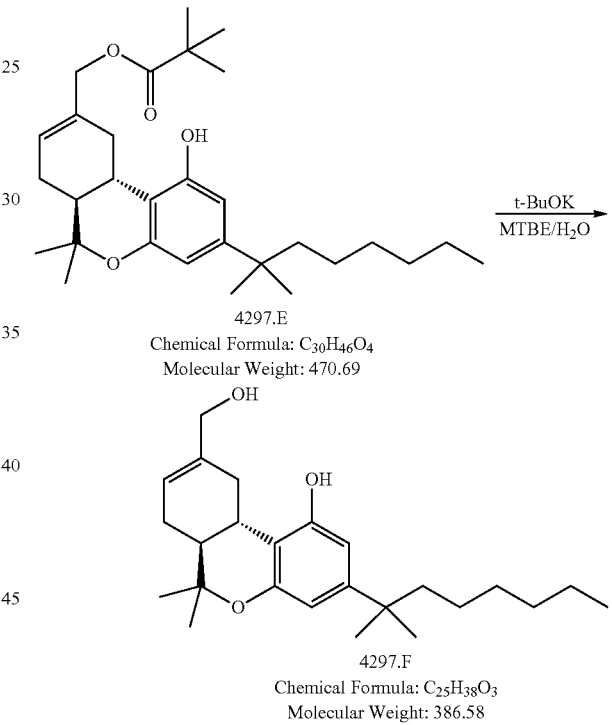

Dexanabinol pivalate ester (4297.E) was subjected to the deprotection reaction with potassium t-butoxide on a 0.23 g scale as follows:

Potassium t-butoxide (0.35 g, 6 equivs) was charged into a 40 mL scintillation vial with septum and nitrogen inlet. The vial was charged with methyl tert-butyl ether (MTBE) (5 mL) and cooled with an ice bath. Next the vial was charged with water (14 μL, 1.6 equiv.). Dexanabinol pivalate ester (4297.E) (Lot#2213-170-3, 78%; 0.226 g, 0.481 mmoles, 1.0 equiv.) was taken up in MTBE (5 mL) and charged into the vial dropwise over 2 minutes by syringe. The resulting brown suspension was then stirred cold for 30 minutes. The bath was then removed and the reaction was stirred at ambient temperature for 4 hours. The reaction was spotted against starting material on TLC and the reaction appeared to be close to complete. The reaction was charged with 3M HCl (2.5 mL) dropwise over several minutes and then was stirred an additional 10 minutes.

The layers were separated by pipet. The MTBE layer was then washed 3× with water (5 mL). The MTBE layer was stored for three days in a freezer and then was concentrated (Rotovap, 30° C.) to give a dark amber liquid.

LC-MS-2213-174-1 Major peak 8.316 mins (90.66% at 210 nm, ES+ 387).

NMR (CDCl$_3$)-2213-174-1Supports desired structure with fairly good purity. Shifts for olefin and exocyclic methylene match previous spectra for dexanabinol.

The crude material was taken up in CH$_2$Cl$_2$ and transferred to a silica flash column. Elution with a step gradient of 10, 20, and 30% ethyl acetate/heptane gave the product spot in good purity by TLC. The fractions containing the major spot were concentrated (Rotovap, 50° C.). The product was then transferred to a tared vial using CH$_2$Cl$_2$ and concentrated (Rotovap, 30-40° C.). Solvents were further chased with two portions of CH$_2$Cl$_2$ to yield 40 mgs of an off-white solid film.

NMR (CDCl$_3$)-2213-174-3 Supports desired structure with very good purity. Wt/wt potency with internal 1,4-dimethoxybenzene gave 95.7%.

The product (4297.F) was isolated in 21.5% yield and 95.7% potency.

EXAMPLE 2

2a) Synthesis of hydroxy verbenone (RTE.1.1) from verbenone

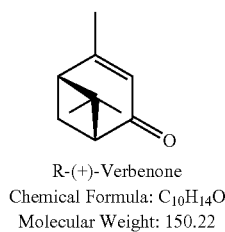

R-(+)-Verbenone
Chemical Formula: C$_{10}$H$_{14}$O
Molecular Weight: 150.22

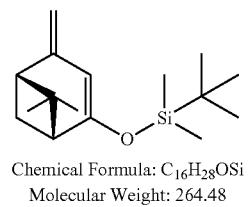

Chemical Formula: C$_{16}$H$_{28}$OSi
Molecular Weight: 264.48

A 10.0 g lot of R-verbenone was submitted to reaction with TBSOTf and triethyl amine as follows:

R-(+)-verbenone (88.4% wt/wt; 10.0 g, 58.8 mmoles) was charged into a round bottom flask with magnetic stirring, temperature probe, addition funnel, and nitrogen inlet as a solution in CH$_2$Cl$_2$ (30 mL). The flask was then charged with CH$_2$Cl$_2$ (470 mL) and cooled with an ice bath (internal temperature 1.3° C.). Triethylamine (16.4 mL, 2.0 equivs) was charged gradually. The reaction was then charged dropwise with tert-butyldimethylsilyl trifluoromethanesulfonate (TBSOTf) (15.5 mL, 1.1 equiv.). The addition was made such that the internal temperature remained <3° C. The resulting solution was stirred cold for 45 mins. A small aliquot was withdrawn, blown dry with nitrogen, and taken up in CDCl$_3$.

NMR (CDCl$_3$)-2213-160-1 1H spectrum supports conversion of the starting material to desired product. A minor multiplet at 5.625 ppm (0.088 H) may be starting olefin or an impurity.

The solution was stirred cold for another 45 mins. Another aliquot was withdrawn for IPC by NMR.

NMR (CDCl$_3$)-2213-160-2 1H spectrum showed 0.079 H of minor olefin material.

The reaction (with continued cooling) was quenched by gradual addition of saturated sodium bicarbonate (125 mL). Internal temperature rose only slightly during the initial dropwise addition and the remainder was added more quickly. The layers were poured off into a separator funnel and the remaining 375 mL of saturated bicarbonate solution was added. After shaking the bottom layer (product, CH$_2$Cl$_2$) was drawn off and the basic layer was extracted with another charge of CH$_2$Cl$_2$ (500 mL.) The bottom layer was again drawn off and a small amount of interfacial layer was left with the upper aqueous layer. The combined organic layers were dried over MgSO$_4$ and concentrated (Rotovap, 30° C.). Obtained 18.02 g or 88.4%.

NMR (CDCl$_3$)-2213-160-3 A&B. $^1$H spectra confirm desired material and also shows ~7% of minor olefin material. Average of two determinations 76.7%

Preparation of tert-butyl(((1R,5S)-6,6-dimethyl-4-methylenebicyclo[3.1.1]hept-2-en-2-yl)oxy)dimethylsilane proceeded to provide the product in 93% yield.

$^1$H NMR data for starting material (Verbenone):

300 MHz NMR, CDCl$_3$ solvent; 5.73 (1H, m, olefinic proton), 2.77-2.84 (1H, m), 2.64 (1H, dt), 2.42 (1H, dt), 2.08 (1H, d), 2.02 (3H, s), 1.50 (3H, s), 1.01(3H, s).

$^1$H NMR data for product [tert-butyl(((1R,5S)-6,6-dimethyl-4-methylenebicyclo[3.1.1]hept-2-en-2-yl)oxy) dimethylsilane][Lot #2213-160-3]:

300 MHz NMR, CDCl$_3$ solvent; 5.20 (1H, m, olefinic proton), 4.49 (2H, dd, 3 Hz, 9 Hz), 2.52-2.57 (1H, m), 2.13 (1H, dt), 1.58 (1H, d, 9 Hz), 1.35 (3H, s), 0.91 (12H, m), 0.18 (6H, m).

The peaks (of interest) used for following/monitoring the reaction are highlighted in bold.

2b) Vinylogous Rubottom Oxidation

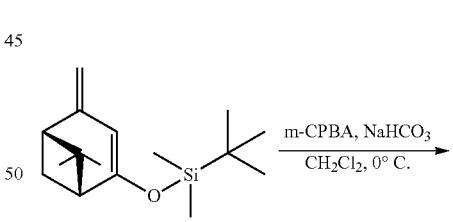

Chemical Formula: C$_{16}$H$_{28}$OSi
Molecular Weight: 264.48

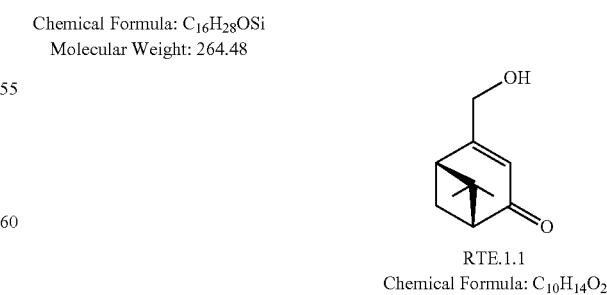

RTE.1.1
Chemical Formula: C$_{10}$H$_{14}$O$_2$
Molecular Weight: 166.22

Intermediate silyldienol ether (tert-butyl(((1R,5 S)-6,6-dimethyl-4-methylenebicyclo[3.1.1]hept-2-en-2-yl)oxy)dimethylsilane) was subjected to the reaction on a 18 g scale using m-chloroperoxybenzoic acid (m-CPBA) and sodium bicarbonate.

The crude intermediate silyl ether (2213-162-3; 18.0 g, 52.0 mmoles) was taken up in $CH_2Cl_2$ (380 mL, 20 volumes) and charged into a jacketed reactor with mechanical stirring, temperature probe, and nitrogen inlet. The solution was then cooled to −9.3° C. internal (chiller −13.2° C.). The solid sodium bicarbonate (13.79 g, 2.2 equivs) was charged in two portions. The reaction was then charged with m-chloroperoxybenzoic acid (m-CPBA) (Sigma-Aldrich, 77%, 12.81 g, 1.2 equivs) in several portions. Internal temperature reached 2.3° C. at end of last charge. The suspension was stirred cold for one hour (internal temperature maintaining <−12° C. A sample was withdrawn and quenched in saturated $Na_2S_2O_3$. After diluting with $CH_2Cl_2$ the layers were separated. The lower (organic) was blown dry with nitrogen and taken up in $CDCl_3$ for NMR.

NMR ($CDCl_3$)-2213-162-1 $^1H$ supports desired product formed with no starting enol ether detected. There was an apparent olefin peak at the shift of the olefin in R-(+)-verbenone. Ratio was ~3:1. It could not be determined if this had hydrolysed in the course of the reaction or on quenching of the aliquot.

The reaction was then quenched in the cold by gradual addition of saturated $Na_2S_2O_3$ (180 mL, 10 volumes). The reactor was allowed to warm until the ice slurry melted, giving a white suspension. The layers were separated and the bottom layer ($CH_2Cl_2$, product) was set aside. The aqueous layer was then extracted 1× with $CH_2Cl_2$ (180 mL, 10 volumes). The combined organic layers were then washed with saturated brine (90 mL, 5 volumes). This dissolved the remaining white suspension. The organic layers were dried over $MgSO_4$ and then concentrated (Rotovap, 30° C.). NMR of crude supports desired structure.

NMR ($CDCl_3$)-2213-162-$^1H$ supports desired structure but shows probable verbenone (quenched silyldienolether) as well (~5:3).

The crude product was taken up in $CH_2Cl_2$ and transferred to a silica flash column. Elution with starting at 10% ethyl acetate/heptane gave two major spots with good apparent purity of the fractions by TLC ($KMnO_4$.) The fractions of each were combined and concentrated (Rotovap, 50° C.). Each material was transferred to a tared vial and residual solvents were chased with portions of $CH_2Cl_2$.

LC-2213-162-3 Major peak 10.117 mins (35.48%) plus peak 12.636 mins (47.92%).

LCMS-2213-162-3 Major peak 4.412 mins (38.51%, ES+ 151,301) plus peak 4.556 mins (38.59%, ES-155/157).

NMR ($CDCl_3$)-2213-162-3 $^1H$ supports recovered verbenone plus co-eluting 3-chlorobenzoic acid. Obtained crude weight 4.19 g with wt/wt potency 47.1% for calculated recovery of 1.97 g (22% recovered verbenone).

LC-2213-162-4 Major peak 3.763 mins (75.40%) plus minor peak 4.779 mins (3.37%) and peak 12.668 mins (17.10%).

LCMS-2213-162-4 Major peak 2.807 mins (75.40%, ES+ 167,333) plus minor peak 3.029 mins (4.29%, ES− 155/157) and peak 4.409 mins (20.30%).

NMR ($CDCl_3$)-2213-162-4 $^1H$ supports the desired (+)-oxy-myrtenol RTE.1.A. Purity is fairly good apart from a trace amount of co-eluting 3-chlorobenzoic acid. Obtained crude weight 4.78 g with wt/wt potency 75.8% for calculated recovery 3.62 g (37% based on starting verbenone, 47% based on recovered verbenone).

$^1H$ NMR data for starting material
[tert-butyl(((1R,5 S)-6,6-dimethyl-4-methylenebicyclo [3.1.1]hept-2-en-2-yl)oxy)dimethylsilane][Lot #2213-160-3]:
300 MHz NMR, $CDCl_3$ solvent; 5.20 (1H, m, olefinic proton), 4.49 (2H, dd, 3 Hz, 9 Hz), 2.52-2.57 (1H, m), 2.13 (1H, dt), 1.58 (1H, d, 9 Hz), 1.35 (3H, s), 0.91 (12H, m), 0.18 (6H, m).

$^1H$ NMR data for product [4-oxo-myrtenol or hydroxyl verbenone] [Lot #2213-162-4]:
300 MHz NMR, $CDCl_3$ solvent; 5.98 (1H, s, olefinic proton), 4.28 (2H, m), 2.82-2.88 (1H, m), 2.65-2.70 (1H, m), 2.39-2.43 (1H, m), 2.11 (1H, d, 9 Hz), 1.51 (3H, s), 1.01 (3H, s).

The peaks (of interest) used for following/monitoring the reaction are highlighted in bold.

2c) Selective 1,2-reduction of (+)-4-oxomyrtenol (RTE.1.1) to (+)-4-hydroxymyrtenol (RTE.1.2A) using Luche conditions (Expt #2213-176)

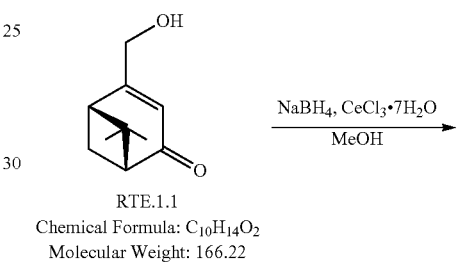

RTE.1.1
Chemical Formula: $C_{10}H_{14}O_2$
Molecular Weight: 166.22

RTE1.2A
Chemical Formula: $C_{10}H_{16}O_2$
Molecular Weight: 168.24

A 0.80 g lot of (+)-4-oxomyrtenol (RTE.1.1) was reduced with $NaBH_4$ and $CeCl_3 \cdot 7H_2O$ as follows:

A 100 mL round bottom flask was equipped with magnetic stirring and nitrogen inlet. The flask was charged with methanol (36 mL, 45 volumes) followed by $CeCl_3 \cdot 7H_2O$ (Sigma-Aldrich; 1.38 g, 1.0 equivs.). The flask was cooled with an ice bath and charged with sodium borohydride (Sigma-Aldrich; 0.138 g, 1.0 equivs.). The 4-oxomyrtenol (2213-162-4, 76%; 0.8 g, 3.66 mmoles) was taken up in methanol (3 mL) and charged into the reaction dropwise. The reaction was stirred cold for 30 minutes and then was stirred at ambient temperature for another one hour. An aliquot was withdrawn and quenched in water. Dichloromethane was added and the bottom layer was drawn off by pipet and checked by TLC (ethyl acetate/n-heptane systems). The reaction appeared to be ~60-70% complete, converting to a new spot corresponding to the diol.

The amber reaction was cooled once again with an ice bath and a charge of sodium borohydride (Sigma-Aldrich; 0.138 g, 1.0 equivs.) was added. The reaction was allowed to warm and was stirred for another 1 hour. TLC now indicated the reaction to be virtually complete.

The flask was charged with water (36 mL) in drops at first and then more rapidly after gas evolution had slowed. After stirring the white, gelatinous suspension was transferred to a separator funnel. The aqueous phase was extracted with $CH_2Cl_2$ (100 ml) and the bottom layer ($CH_2Cl_2$, product) was drawn off. Separation of the layers was only partial due to the gelatinous suspension. The aqueous layer was then extracted with $CH_2Cl_2$ (100 mL) and the bottom layer was drawn off and combined with the first extraction.

The combined organic layers were washed with saturated brine solution (25 mL). The organic layer was dried over $MgSO_4$ and concentrated (Rotovap, 30-40° C.) to give a white solid. The aqueous layers were checked by TLC and there seemed to be only traces of the major product spot. Obtained 0.67 g of white solid.

NMR ($MeOD_4$)-2213-176-4 Supported the desired crude product structure. The purity of the crude product appeared to be good.

NMR Potency ($MeOD_4$ with 1,4-dimethoxybenzene)-84.6% (average of two).

Calculated yield after correction 92.1%.

LC-2213-176-3 Major peak 3.887 (~100%).

LC-MS-2213-176-3 Major peak 2.887 mins (97.73%) (no parent ion).

The reduction of (+)-4-oxomyrtenol (RTE.1.1) using borohydride and $CeCl_3 \cdot 7H_2O$ gave (+)-4-hydroxymyrtenol (RTE.1.2A) in 85% potency and 92% as a crude product.

2d) Coupling of 4-hydroxy-myrtenol (RTE.1.2A) with DMHR to prepare Dexanabinol (4297.F)

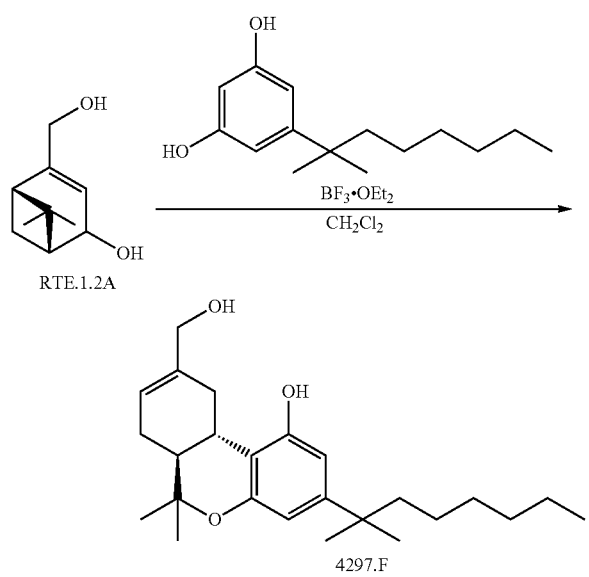

4-Hydroxy-myrtenol (RTE.1.2A) was subjected to the coupling reaction with dimethylbicyclo[3.1.1]hept-2-ene-2-methanol (DMHR) on a 0.4 g scale as follows:

RTE.1.2A (Lot#2213-176-5, 84.6%; 0.40 g, 2.01 mmoles, 1.0 equiv.) was charged into a 40 mL scintillation vial with septum and nitrogen inlet. The vial was charged with DMHR (Lot#14A1-049A; 0.43 g, 0.9 equiv.). Next the vial was charged with $CH_2Cl_2$ (10 mL) and the suspension was cooled with an ice/salt bath. The reaction was then charged with $BF_3$.etherate (0.84 mL, 3.3 equivs) added dropwise over 2 minutes by syringe. The resulting brown solution was then stirred cold for 1 hour (reaching a bath temperature of −10° C.). An aliquot was withdrawn and quenched in a small volume of water. After extracting with $CH_2Cl_2$ progress was checked by TLC in 3 systems (all ethyl acetate/heptane). There appeared to be no RTE.1.2A remaining. There was some unreacted DMIHR slightly separated from the new spot.

After another 45 minutes stirring below −10° C. another aliquot was withdrawn and quenched in a small volume of water. After extracting with $CH_2Cl_2$ progress was checked by TLC in 3 systems (all ethyl acetate/heptane). Result was similar to above.

The reaction was then quenched in the cold by gradual addition of water (5 mL, 5 volumes). The reaction was allowed to warm with vigorous stirring. The layers were separated by pipet and the bottom layer ($CH_2Cl_2$, product) was set aside. The aqueous layer was then extracted 1× with $CH_2Cl_2$ (10 mL, 5 volumes.) The combined organic layers were then washed with saturated sodium bicarbonate (5 mL, 5 volumes). Next the organic layer was washed with 25% sodium hydroxide (0.5 mL). The reaction turned a dark purple colour. After separating these layers the organic layer was adjusted to pH of ·2 with dropwise addition of 1 N HCl. This discharged the dark colour and returned the reaction to beige. The lower layer was removed by pipet and the acid layer set aside.

Then the organic layer were washed 2× with water (5 mL). The organic layer was then concentrated (Rotovap, 30-40° C.).

NMR ($CDCl_3$)-2213-178-2 Supported the desired crude product structure.

The crude product was taken up in $CH_2Cl_2$ and a few drops of methanol and transferred to a silica flash column. Elution with a step gradient of 10, 20, and 30% ethyl acetate/heptane gave elution of a major spot of the correct Rf. The spot was well separated from any excess DMHR but appeared to co-elute with a dark colour. Fractions containing the product spot were concentrated (Rotovap, 50° C.). The material was transferred to a tared vial and residual solvents were chased with portions of $CH_2Cl_2$. JMPS lot 2213-178-3; 0.27 g of dark semi-solid.

NMR ($CDCl_3$)-2213-178-4 Spectrum supports desired structure with some impurities. Potency determination by wt/wt (1,4-dimethoxybenzene) gave 67.6%. Yield calculated 23.6% from potency data.

The invention claimed is:

1. A method of preparing a compound of formula I, and optical isomers thereof:

in which $R^1$ is hydrogen;

said method consisting of oxidising verbenone (4,6,6-trimethylbicyclo[3.1.1]hept-3-en-2-one) and optical isomers thereof:

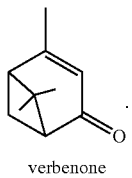
verbenone

2. The method according to claim 1 wherein the compound of formula I is the (R)-isomer, Ia:

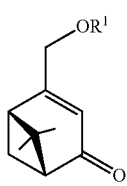

Ia

3. The method according to claim 1 wherein the compound of formula I is the (S)-isomer, Ib:

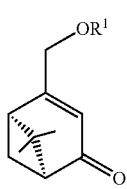

Ib

4. The method according to claim 1 in which R¹ is hydrogen and the method includes a step of protection of (+)-4-oxomyrtenol.

5. A method of preparing a 9-(hydroxymethyl)-6,6-dimethyl-3-(2-methyloctan-2-yl)-6a,7,10,10a-tetrahydrobenzo[c]chromen-1-ol cannabinoid which comprises reacting a compound of formula I in which R¹ is hydrogen, with 5-(1,1-dimethylheptyl)resorcinol.

6. A method of preparing a 3-substituted cannabinoid compound which comprises reacting a compound of formula I with 5-substituted resorcinol.

7. A method according to claim 6 which comprises reacting a compound of formula I with 5-alkyl resorcinol.

8. A method of preparing a 9-(hydroxymethyl)-6,6-dimethyl-3-(2-methyloctan-2-yl)-6a,7,10,10a-tetrahydrobenzo[c]chromen-1-ol cannabinoid which comprises the steps of:
  (i) oxidising a verbenone and optical isomers thereof;

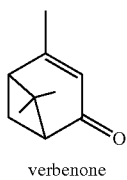
verbenone to produce 4-oxomyrtenol or protected 4-oxomyrtenol;
  (ii) optionally protecting the hydroxy group of 4-oxomyrtenol;
  (iii) reacting the 4-oxomyrtenol, or a protected derivative thereof, with 5-(1,1-dimethylheptyl)resorcinol to produce a 9-(hydroxymethyl)-6,6-dimethyl-3-(2-methyloctan-2-yl)-6a,7,10,10a-tetrahydrobenzo[c]chromen-1-ol cannabinoid, or a protected derivative thereof; and
  (iv) optionally deprotecting the protected derivative of the 9-(hydroxymethyl)-6,6-dimethyl-3-(2-methyloctan-2-yl)-6a,7,10,10a-tetrahydrobenzo[c]chromen-1-ol cannabinoid.

9. The method according to claim 8 wherein (+)-4-oxomyrtenol is reacted with 5-(1,1-dimethylheptyl)resorcinol to produce dexanabinol.

10. The method according to claim 8 wherein the cannabinoid is dexanabinol, said method comprising the steps of:
  (i) oxidising (R)-verbenone to produce (+)-4-oxomyrtenol or protected (+)-4-oxomyrtenol;
  (ii) optionally protecting the hydroxy group of (+)-4-oxomyrtenol;
  (iii) reacting the (+)-4-oxomyrtenol, or a protected derivative thereof, with 5-(1,1-dimethylheptyl)resorcinol to produce dexanabinol, or a protected derivative thereof; and
  (iv) optionally deprotecting the protected derivative of dexanabinol.

11. The method according to claim 8 wherein (−)-4-oxomyrtenol is reacted with 5-(1,1-dimethylheptyl)resorcinol to produce HU-210.

12. The method according to claim 8 wherein the cannabinoid is HU-210, said method comprising the steps of:
  (i) oxidising (S)-verbenone to produce (−)-4-oxomyrtenol or protected (−)-4-oxomyrtenol;
  (ii) optionally protecting the hydroxy group of (−)-4-oxomyrtenol;
  (iii) reacting the (−)-4-oxomyrtenol, or a protected derivative thereof, with 5-(1,1-dimethylheptyl)resorcinol to produce HU-210, or a protected derivative thereof; and
  (iv) optionally deprotecting the protected derivative of HU-210.

13. A method of preparing a compound of formula I, and optical isomers thereof, which comprise formation of a dienol intermediate of formula II, and optical isomers thereof:

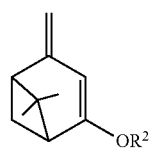

II in which R² is a protecting group.

14. A method of preparing a 9-(hydroxymethyl)-6,6-dimethyl-3-(2-methyloctan-2-yl)-6a,7,10,10a-tetrahydrobenzo[c]chromen-1-ol cannabinoid which comprises the steps of:
  (i) oxidising a compound of formula II and optical isomers thereof;

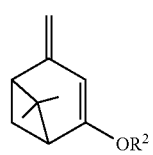

II in which R² is a protecting group;

to produce 4-oxomyrtenol or protected 4-oxomyrtenol;

(ii) optionally protecting the hydroxy group of 4-oxomyrtenol;

(iii) reacting the 4-oxomyrtenol, or a protected derivative thereof, with 5-(1,1-dimethylheptyl)resorcinol to produce 9-(hydroxymethyl)-6,6-dimethyl-3-(2-methyloctan-2-yl)-6a,7,10,10a-tetrahydrobenzo[c]chromen-1-ol cannabinoid, or a protected derivative thereof; and (iv) optionally deprotecting the protected derivative of 9-(hydroxymethyl)-6,6-dimethyl-3-(2-methyloctan-2-yl)-6a,7,10,10a-tetrahydrobenzo[c]chromen-1-ol cannabinoid.

15. The method according to claim 14 wherein the cannabinoid is (6aS,10aS)-9-(hydroxymethyl)-6,6-dimethyl-3-(2-methyloctan-2-yl)-6a,7,10,10a-tetrahydrobenzo[c]chromen-1-ol, dexanabinol.

16. The method according to claim 14 wherein the cannabinoid is (6aR,10aR)-9-(hydroxymethyl)-6,6-dimethyl-3-(2-methyloctan-2-yl)-6a,7,10,10a-tetrahydrobenzo[c]chromen-1-ol, HU-210.

* * * * *